US005833985A

United States Patent [19]
Ball et al.

[11] Patent Number: 5,833,985
[45] Date of Patent: Nov. 10, 1998

[54] BISPECIFIC MOLECULES FOR USE IN INDUCING ANTIBODY DEPENDENT EFFECTOR CELL-MEDIATED CYTOTOXICITY

[75] Inventors: Edward D. Ball, Wexford, Pa.; Michael W. Fanger, Lebanon, N.H.

[73] Assignee: Medarex, Inc., Annandale, N.J.

[21] Appl. No.: 451,194

[22] Filed: May 26, 1995

Related U.S. Application Data

[62] Division of Ser. No. 207,344, Mar. 7, 1994, abandoned.

[51] Int. Cl.$^6$ ...................... A61K 39/385; A61K 39/395; C12P 21/08; C07K 16/46
[52] U.S. Cl. .................................. 424/134.1; 424/195.11; 424/180.1; 424/198.1; 530/387.3; 530/387.7; 530/388.22; 530/399
[58] Field of Search .............................. 424/134.1, 180.1, 424/198.1, 195.11; 530/399, 388.1, 387.3, 387.7, 388.22

[56] References Cited

U.S. PATENT DOCUMENTS

| 4,676,980 | 6/1987 | Segal et al. | 424/130.1 |
|---|---|---|---|
| 4,954,617 | 9/1990 | Fanger et al. | 530/387.1 |
| 5,109,115 | 4/1992 | Cuttitta et al. | 530/387.1 |

FOREIGN PATENT DOCUMENTS

| WO 88/00052 | 1/1988 | WIPO . |
|---|---|---|
| WO 91/00360 | 1/1991 | WIPO . |

OTHER PUBLICATIONS

Trepel et al BBRC 156(3) 1383–9 (1988).

Maruno et al Life Sci 52/24 (PL–267–PL–271 1993.

Connor et al J of Immunol. vol. 1145 1483–1489, 1990.

Fangei et al (1989) pp. 92–99.

Woodhouse et al Cancer Res 49:2766–2772 (1989).

Anderson et al., "Monoclonal Antibodies to Fc Receptors for IgG on Human Mononuclear Phagocytes", *The Journal of Biological Chemistry*, vol. 261, No. 27, pp. 12856–12864, (1986).

Karpovsky et al., "Production of Targeted–Specific Effector Cells Using Hetero–Cross–Linked Aggregates Containing Anti–Target Cell and Anti–Fcγ Receptor Antibodies", *J. Exp. Med.*, vol. 160, pp. 1686–1701, (1984).

Link and Weiner, "Production and Characterization of a Bispecific IgG Capable of Inducing T–Cell–Mediated Lysis of Malignant B Cells", *Blood*, vol. 81, No. 12, pp. 3343–3349, (1993).

Mokotoff et al., "Synthesis and Biological Evaluation of Novel Potent Antagonists of the Bombesin/Gastrin Releasing Peptide Receptor", *J. Med. Chem.*, vol. 35, pp. 4696–4703, (1992).

Moody et al., "Growth Factor and Peptide Receptors in Small Cell Lung Cancer", *Life Sciences*, vol. 52, pp. 1161–1173, (1993).

Pan et al., "Regulation of the Steady State Level of FcγRI mRNA by IFN–γ and Dexamethasone in Human Monocytes, Neutrophils, and U–937 Cells", *The Journal of Immunology*, vol. 145, pp. 267–275, (1990).

Shen et al., "Heteroantibody–Mediated Cytotoxicity: Antibody to the High Affinity Fc Receptor for IgG Mediates Cytotoxicity by Human Monocytes that is Enhanced by Interferon–γ and is not Blocked by Human IgG", *the Journal of Immunology*, vol. 137, No. 11, pp. 3378–3382, (1986).

Thomas et al., "Antitumoral Activity of Bombesin Analogues on Small Cell Lung Cancer Xenografts: Relationship with Bombesin Receptor Expression", *Cancer Research*, vol. 52, pp. 4872–4877, (1992).

Trail et al., "Cure of Xenografted Human Carcinomas by BR96–Doxorubicin Immunoconjugates", *Science*, vol. 261, pp. 212–215, (1993).

Vallera D. A., "Immunotoxins: Will Their Clinical Promise Be Fulfilled?", *Blood*, vol. 83, No. 2, pp. 309–317, (1994).

Weiner et al., "Binding and Cytotoxicity Characteristics of the Bispecific Murine Monoclonal Antibody 2B1", *The Journal of Immunology*, vol. 151, No. 5, pp. 2877–2886, (1993).

Eisenthal et al. "The Effect of Various Cytokines on the In Vitro Induction of Antibody–Dependent Cellular Cytotoxicity in Murine Cells", *The American Association of Immunologists*, vol. 142, No. 7, pp. 2307–2313 (1989.

Primary Examiner—Lila Feisee
Assistant Examiner—Geetha P. Bansal
Attorney, Agent, or Firm—Lahive & Cockfield, LLP

[57] ABSTRACT

Bispecific molecules comprising a non-immunoglobulin tumor cell specific ligand and an antibody which binds the Fc receptor of an effector cell at a site that is not inhibited by endogenous immunoglobulin are disclosed. The bispecific molecules can be used to induce a specific antibody dependent effector cell-mediated cytotoxicity against tumor cells, such as small cell lung carcinoma (SCLC) cells, either in vivo or in vitro.

8 Claims, 7 Drawing Sheets

BISPECIFIC MOLECULES FOR USE IN INDUCING ANTIBODY DEPENDENT EFFECTOR CELL-MEDIATED CYTOTOXICITY

This application is a divisional application of Ser. No. 08/207,344 filed on Mar. 7, 1994, now abandoned. The contents of all of the aforementioned application(s) are hereby incorporated by reference.

BACKGROUND OF THE INVENTION

Several types of effector cells, such as monocytes, neutrophils, and natural killer (NK) cells, have surface receptors that bind the Fc portion of immunoglobulins. When such cells encounter target cells that have been opsonized with immunoglobulin antibodies, they form conjugates, and either lyse or phagocytose the target cells, depending upon the effector cell type, the target cell type and the specific Fc receptor type (FcR) involved.

It has been demonstrated that target cell conjugation with an effector cell and lysis can also be induced by a covalently cross-linked bispecific heteroantibody made up of both anti-Fc receptor antibody and antibody directed against a target cell epitope. When effector cells bind such heteroaggregates to their Fc receptor, they can specifically bind and lyse target cells which have not been opsonized, but which express the appropriate target antigen (See e.g. U.S. patent application Ser. No. 972,871; Karpovsky et al. (1984) *J. Exp. Med.* 160:1686–1701). Segal et al. have reported cytolysis of tumor cells by mouse monocytes with an attached heteroantibody which joins the Fc receptor of the monocyte on one end with tumor cell epitopes on the other end (See U.S. Pat. No. 4,676,980). Recently, a variety of bispecific monoclonal antibodies and immunotoxins have been shown to confer antitumor effects in vitro as well in vivo (See e.g., World Patent No: 9208892; Pan et al (1990) *J. Immunol.*, 145:267–275; Trail et al. (1993) *Science* (Washington, D.C.), 261:212–215; Weiner et al. (1993) *J. Immunol.*, 151:2877–2886; Link et al. (1993) *Blood*, 81:3343–3349; and Vallera, D. A. (1994) *Blood*, 83:309–317).

The binding of a heteroantibody to FcR is mediated by the Fc region of the antibody. This binding is ordinarily susceptible to inhibition by physiological concentrations of immunoglobulin. However, monoclonal antibodies, which bind to a site on the Fc receptor distinct from the binding site for endogenous immunoglobulin, have been produced (see, for example, Anderson et al., *J. Biol. Chem.* 261:12856 (1986); and Shen et al.,*J. Immunol.* 137:3378–3382 (1986)). These antibodies are useful as the effector-specific moiety of heteroantibodies, because serum immunoglobulin does not interfere with targeted effector cell killing.

Heteroantibodies are large in size and therefore present certain difficulties when used clinically. Smaller molecules capable of binding to target cells and effector cells and initiating ADCC would be useful.

SUMMARY OF THE INVENTION

In one aspect, the invention relates to a bispecific molecule comprising a target cell specific ligand and an antibody or functional antibody fragment specific for an effector cell. In a preferred embodiment, the antibody or functional antibody fragment is specific against the Fc receptors (FcR) of effector cells. Most preferably the bispecific molecules of the instant invention comprise an effector cell specific antibody or functional fragment that binds to the FcR at a site distinct from the binding site for endogenous immunoglobulin; and a target cell specific ligand that binds to a tumor cell receptor, most preferably the gastrin-releasing peptide (GRP) receptor expressed by small cell cancer of lung (SCCL) cells.

In other aspects, the invention relates to methods for making the novel bispecific molecules and to methods of using the molecules therapeutically, e.g. to induce an antibody dependent effector cell-mediated cytotoxicity (ADCC) or prophylactically, as a vaccine.

The novel bifunctional molecules described herein are generally of a smaller size than heteroantibodies and the target cell specific ligand binding to target cell mimics normal physiology. Therefore the instant bifunctional molecules offer certain therapeutic advantages (e.g. reduced immunogenicity).

The above discussed and many other features and advantages of the present invention will become better understood by reference to the following detailed description when taken in conjunction with the accompanying drawings.

DETAILED DESCRIPTION OF THE INVENTION

Figure 1:
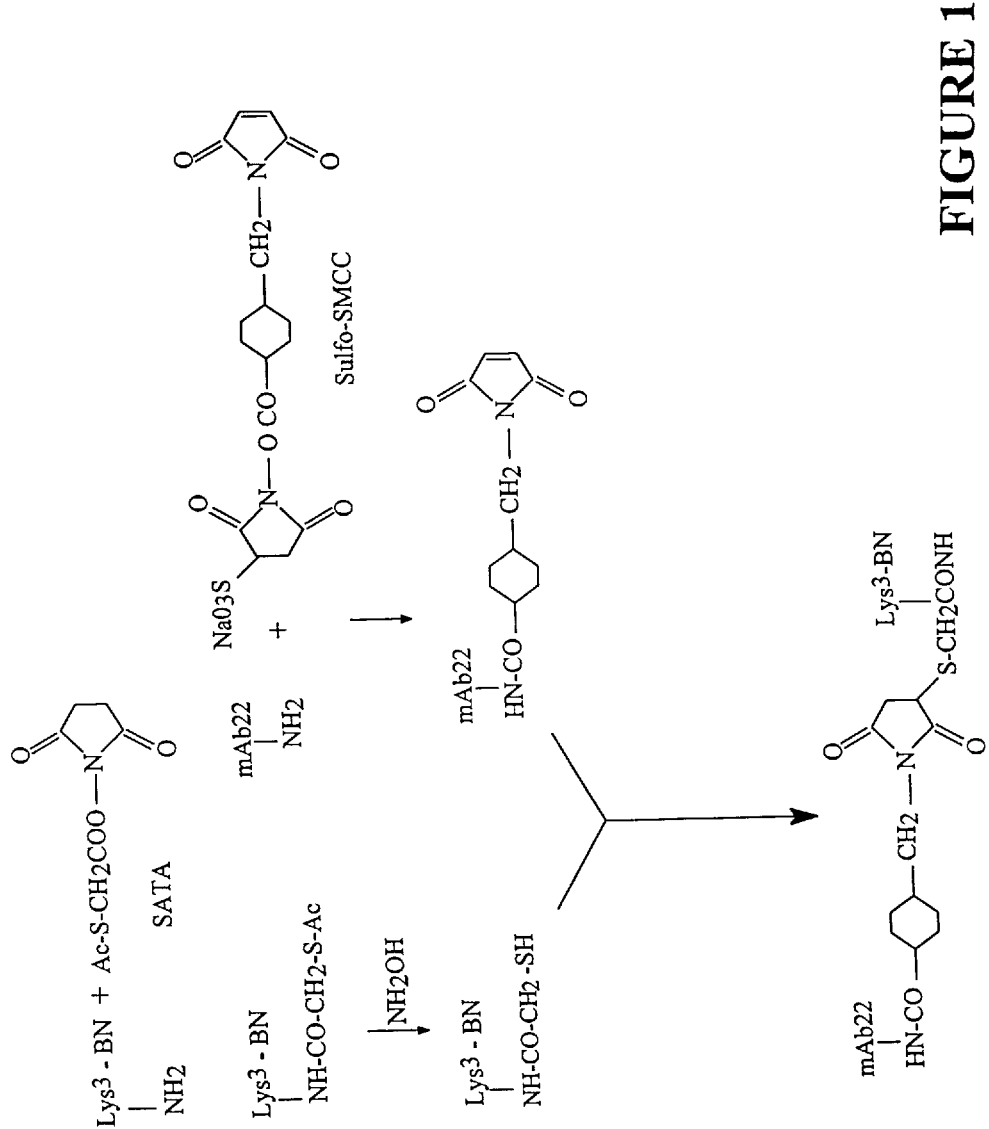
FIG. 1 shows the scheme for conjugating Lys$^3$-bombesin and mAb 22 or F(ab')$_2$ fragments thereof.
Figure 2A:
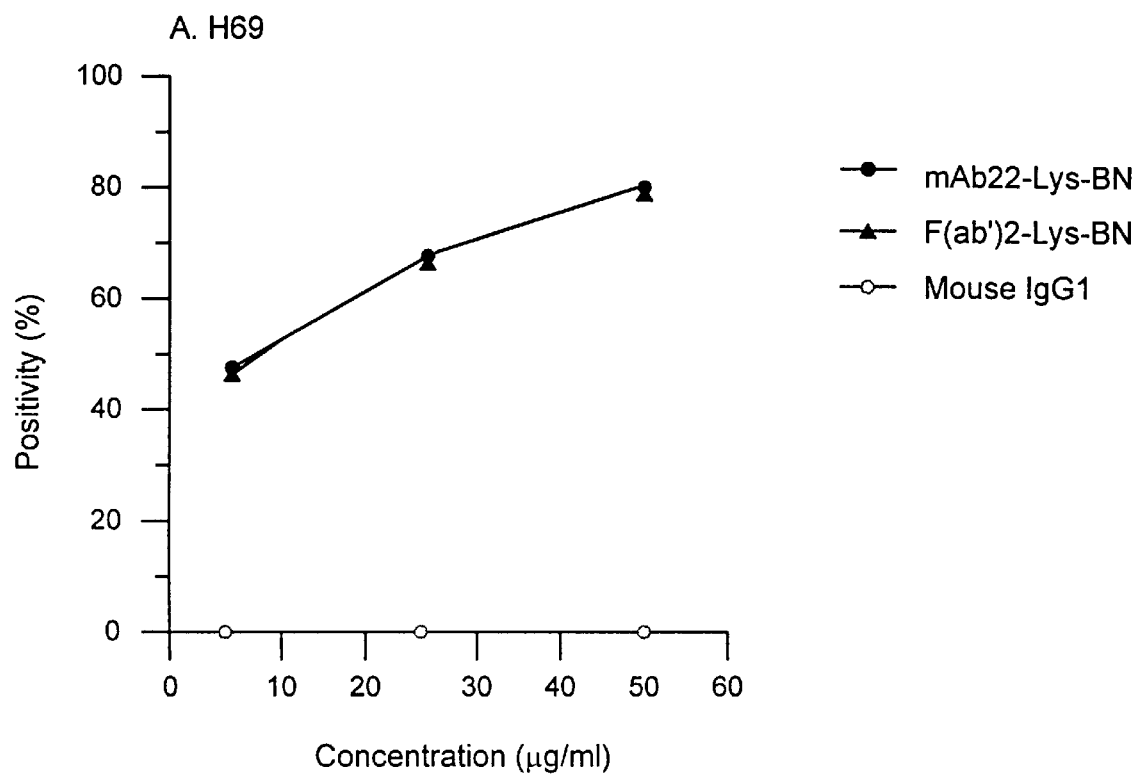
FIG. 2 shows a flow cytometry analysis of bispecific molecule (Lys$^3$-bombesin-mAb 22) binding to four small cell cancer of lung (SCCL) cell lines, SHP77, H69, DMS273, and H345.
Figure 2B:
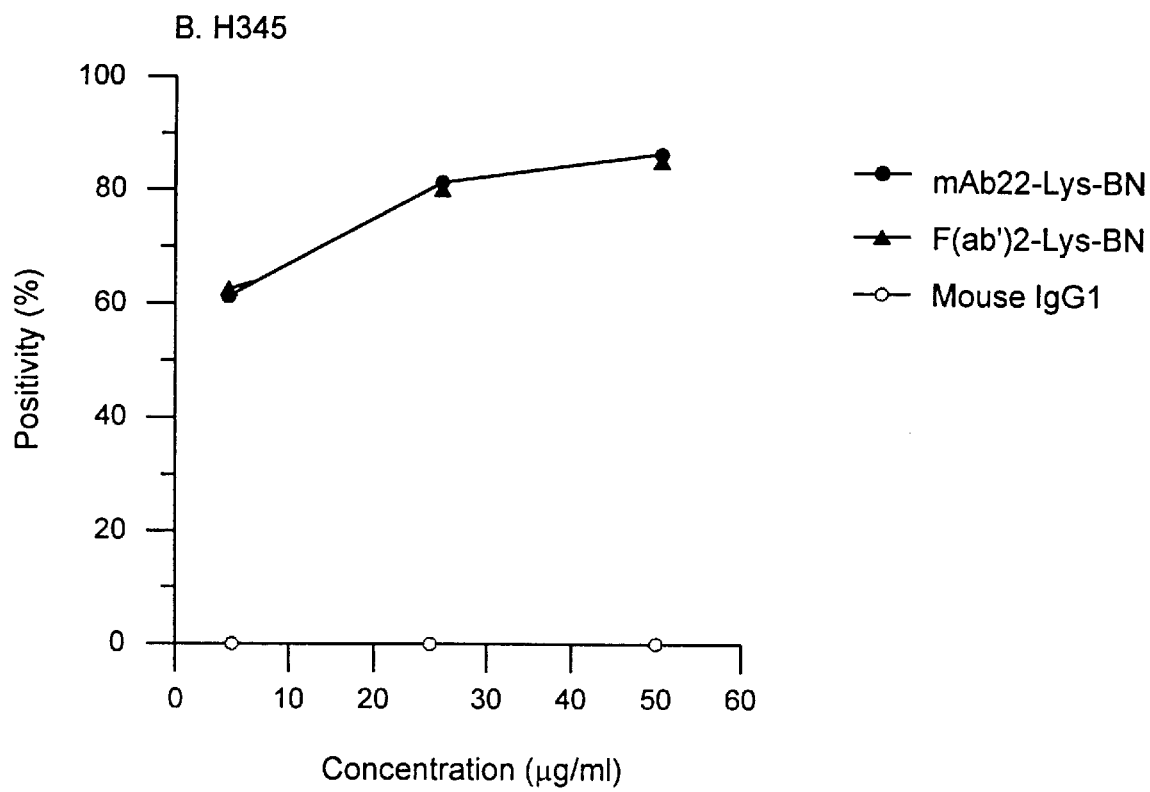
Figure 2C:
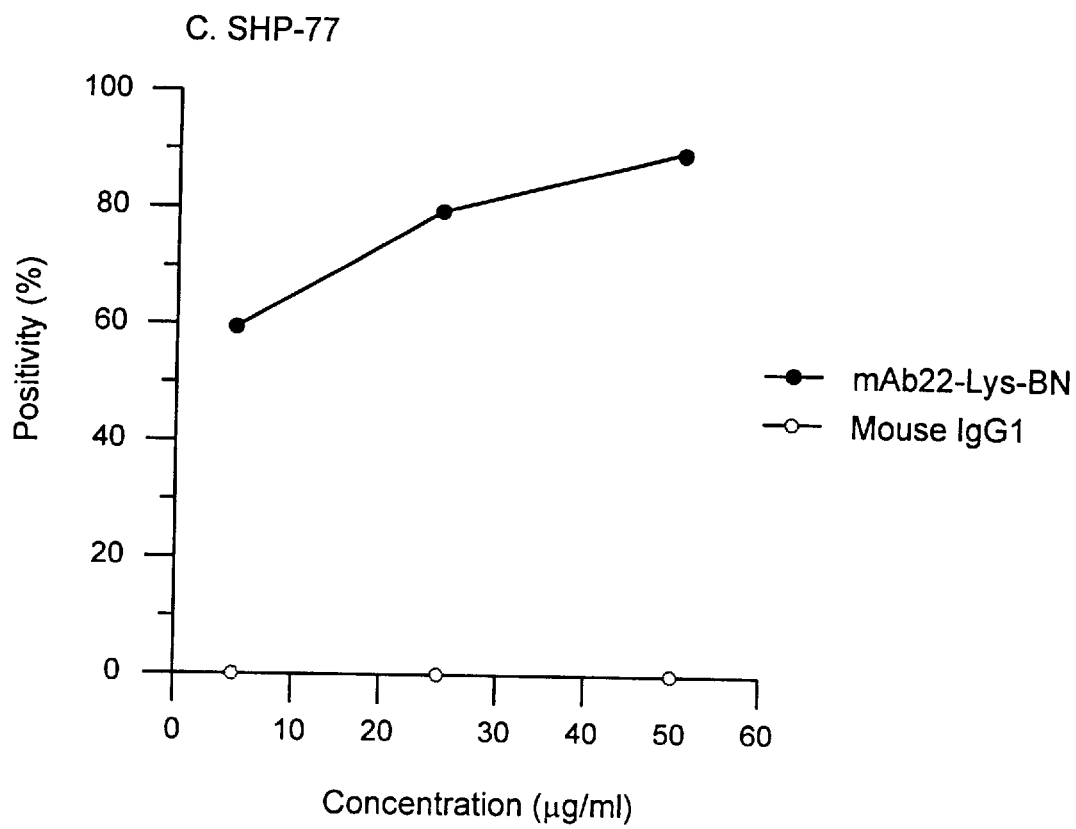
Figure 2D:
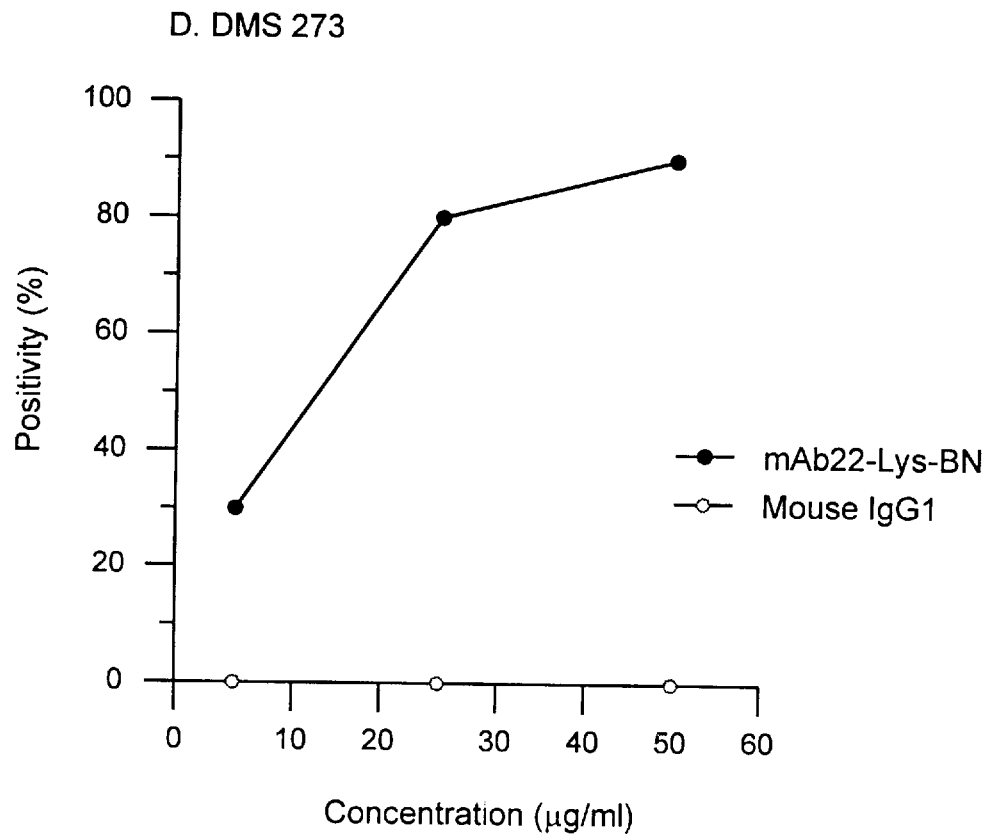

This invention is based on the surprising finding that ligands specific for a particular target cell can be useful for initiating a specific antibody-dependent effector cell-mediated cytotoxicity against the target cell (ADCC). In one aspect, the invention features bispecific molecules comprising a ligand specific for a target cell and an antibody or functional antibody fragment specific for an effector cell.

As used herein, the following terms and phrases shall be defined as follows: "bispecific molecule" shall mean a molecule having an antibody portion that is capable of binding an Fc receptor (FcR) on a effector cell; and a ligand portion that is capable of being bound by a receptor or antibody on a target cell.

"Target cell specific ligand" as used herein refers to molecules (e.g. peptides, polypeptides or proteins) that specifically interact with a target cell, for example by way of a target cell surface receptor or antibody. Preferred ligands of the present invention bind to predominantly with target cells and not other cells when administered in vivo. Preferably a ligand is a member of a binding pair with a receptor or antibody that is expressed predominantly by the target cell.

In a preferred embodiment of the invention, the target cell specific ligand is a ligand for the gastrin-releasing peptide (GRP) receptor expressed by small cell cancer of lung (SCCL) cells. As shown herein, GRP receptors of SCCL cells specifically bind GRP, and analogue, bombesin, a fourteen amino acid peptide which contains a carboxy-terminal heptapeptide sequence identical to that of GRP. Accordingly, preferred ligands of the present invention include bombesin, gastrin releasing peptide (GRP), and functional fragments or analogues thereof. The term fragments or analogues thereof is intended to include amino acid sequences which differ by one or more amino acid substitutions, additions or deletions from the full length native bombesin or GRP protein, such as allelic variants. Preferred fragments and analogues of bombesin and GRP have the ability to bind to the bombesin/GRP receptor of SCCL cells and are at least about 50% homologous, more preferably about 60% homologous, and most preferably at least about 70% homologous with the amino acid sequence of native bombesin or GRP. Peptides having the ability to bind to the bombesin/GRP receptor of SCCL cells and having at least about 90%, more preferably at least about 95%, and most preferably at least about 98–99% homology with the amino acid sequence of native bombesin or GRP are also within the scope of the invention. Homology refers to sequence similarity between two peptides having the ability to bind to the bombesin/GRP receptor of SCCL cells. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

SCCL is a neuroendrocrine tumor that in addition to bombesin/GRP requires other hormonal growth factors for proliferation. These other growth factors include, for example, insulin-like growth factor I, transferrin, vasoactive intestinal peptide, neurotensin, neuromedin B, neurophysin, tumor necrosis factor, transforming growth factor alpha, platelet derived growth factor, the transferin receptor and other peptides. Some of the receptors for these growth factors have been shown to be expressed on SCCL cell surface. Therefore these growth factors can also be used as target cell specific ligands in the instant invention. Bispecific molecules of the present invention formed with different ligands specific for a particular target cell, such as those described above for SCCL cells, can be administered alone or concurrently with one another to induce target cell death. Because each growth factor may stimulate a different signal transduction pathway, concurrent administration of the bispecific molecules may also have a synergistic effect.

Ligands of the present invention also include antagonists against receptors of target cells. Antagonist ligands provide an additional therapeutic advantage of inhibiting the growth of target cells upon binding, potentially even in the absence of effector cells. In fact, some antagonists against GRP receptors have been shown to possess very potent activity in inhibiting the growth of SCCL cells in vitro. However, they are quickly degraded by serum proteases before they can reach the target site, for example a tumor site, in vivo (see Moody et al. (1993) *Life Science* 52:1161–1173). However, the presence of small peptide antagonists in a bispecific molecule of the present invention greatly retards their degradation in vivo. Therefore, the present invention also provides the advantage of increasing the efficacy of target cell receptor antagonists when the antagonists are used as ligands in the bispecific molecule of this invention. Methods for making antagonists of the bombesin/GRP receptor are disclosed for example in Mokotoff et al. *J. Med Chem.* 35:4696–4703 (1992).

In addition to SCCL other "target cells" include any tumor cell which expresses a specific receptor or antibody to which a ligand can be generated. Such target cells can for example, myeloid leukemia, ovarian carcinoma or colon carcinoma cells. Other types of undesirable cells that can be targeted by the bispecific molecule of the present invention include, for example, auto-antibody producing lymphocytes for treatment of an autoimmune disease or an IgE producing lymphocyte for treatment of an allergy. The target can also be a microorganism (bacterium or virus) or a soluble antigen (such as rheumatoid factor or other auto-antibodies).

The phrase "effector cell specific antibody" as used herein refers to an antibody or functional antibody fragment. Preferred antibodies for use in the subject invention bind the Fc receptor of effector cells at a site which is not bound by endogenous immunoglobulin. Most preferably, the anti-Fcγ receptor antibody is a human monoclonal antibody, the binding of which is not blocked by human immunoglobulin G (IgG). The production and characterization of these preferred monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, 12301 Parklawn Drive, Rockville, Md. 20852 ATCC Accession No. HB9469 deposited on Jul. 1, 1987. The hybridoma producing mAb 22 is available from the American Type Culture Collection, ATCC Accession No. HB12147. Anti-FcγRI mAb 22, F(ab')$_2$ fragments of mAb 22, and can be obtained from Medarex, Inc. (Annandale, N.J.).

Fragments of anti-FcR antibodies can also be used in the bispecific molecule of the present invention. For example, as shown in the following example, bispecific molecules between Lys$^3$-bombesin and F(ab')$_2$ fragments of mAb 22 have been constructed and found to exhibit a similar binding profile to both target and effector cells and are only slightly less active in inducing cytotoxicity against SCCL cells as compared to bispecific molecules between Lys$^3$-bombesin and the whole mAb 22 (See Tables 1, 4, and 5). Furthermore, since antibody fragments, such as F(ab')$_2$ fragments, are smaller than whole antibody molecules, they may more readily reach tumor sites in vivo and therefore be of greater clinical utility.

The bispecific molecules of the present invention can be prepared by conjugating (e.g. ionically or covalently) the ligand and the antibody or functional antibody fragment using any method known in the art. For example, a variety of coupling or cross-linking agents can be used to covalently conjugate the target cell specific ligand and the effector cell specific antibody. Examples of cross-linking agents include protein A, carboimide, N-succinimidyl-S-acetyl-thioacetate (SATA), N-succinimidyl-3-(2-pyridyldithio) propionate (SPDP), and sulfosuccinimidyl 4-(N-maleimidomethyl) cyclohexane-1-carboxylate (sulfo-SMCC) (see e.g., Karpovsky et al. (1984) *J. Exp. Med.* 160:1686; Liu, M. A. et al. (1985) *Proc. Natl. Acad. Sci. USA* 82:8648. Other methods include those described by Paulus (*Behring Inst. Mitt.*

(1985) No. 78, 118–132); Brennn et al. (*Science* (1985) 229:81–83), and Gennie et al. (*J. Immunol.* (1987) 139:2367–2375). Preferred conjugating agents are SATA and sulfo-SMCC, both available from Pierce Chemical Co. (Rockford, Ill.).

Effector cells for inducing ADCC against a target cell include human leukocytes, macrophages, monocytes, activated neutrophils, and possibly activated natural killer (NK) cells and eosinophils. Preferred effector cells express FcγRI and include, for example, monocytes and activated neutrophils. Expression of FcγRI has been found to be up-regulated by interferon gamma (IFN-γ). This enhanced expression increases the cytotoxic activity of monocytes and neutrophils against target cells, such as SCCL cells. Accordingly, effector cells are preferably activated with (IFN-γ), or other cytokines (e.g. as tumor necrosis factor, lymphotoxin, colony stimulating factor, and interleukin-2) to increase the presence of FcγRI on the surface of the cells prior to being contacted with a bispecific molecule of the present invention.

The bispecific molecules of the present invention can be used to induce antibody-dependent effector cell-mediated cytotoxicity (ADCC) against the target cell. To this end, bispecific molecules of the present invention can be administered freely in a physiologically acceptable solution or can first be coupled to an effector cell, forming an "activated effector cell", prior to being administered to a subject. "Activated effector cell", as used herein, is intended to include an effector cell, as previously defined, linked to a bispecific molecule, as previously defined, so that the effector cell is brought into contact with a particular target cell via a specific ligand-mediated linkage.

Activated effector cells can be administered in vivo as a suspension of cells in a physiologically acceptable solution. The number of cells administered can be in the order of $10^8$–$10^9$, but will vary depending on the therapeutic purpose. In general, the amount will be sufficient to obtain localization of the effector cell at the target cell, and to effect killing of the cell by ADCC and/or phagocytosis. The term physiologically acceptable solution, as used herein, is intended to include any carrier solution which stabilizes the targeted effector cells for administration in vivo including, for example, saline and aqueous buffer solutions, solvents, antibacterial and antifungal agents, isotonic agents, and the like.

Accordingly, another aspect of the present invention provides a method of inducing a specific ADCC against a cell in a subject, comprising administering to the subject the bispecific molecule or activated effector cell of the invention in a physiologically acceptable medium. Routes of administration can vary and include intravenous, intramuscular, and intraperitoneal administration. Prior to or concurrent with administration of the bispecific molecule, the subject may be treated in a manner resulting in increased expression in the target cells of the particular receptor or antibody to which the target cell specific ligand of the bispecific molecule will bind. For example, the subject may be given an agent that upregulates expression of the particular receptor or antibody on the target cell surface. In a preferred embodiment of the invention, a bispecific molecule comprising bombesin or an analogue thereof coupled to a human anti-FcR monoclonal antibody, is administered alone or coupled to an effector cell (i.e. an activated effector cell) to a subject afflicted with small-cell lung cancer to induce ADCC against SCCL cells.

A further aspect of the invention provides a method for using the bispecific molecules as an immunogen. For example, where the target specific ligand is an autocrine growth factor, a bispecific molecule comprising the autocrine growth factor ligand can be administered prophylactically to prevent or retard proliferation of the target cell. For use as a vaccine, bispecific molecules of the instant invention can be administered in a pharmaceutically acceptable solution at a dosage that will evoke an immune response against the target specific ligand. The optimum dose may vary depending on factors such as the immune status of the host. In most cases, the dose of target specific ligand required to elicit an immune response (as determined by any standard method for assessment of immune response) should be lower than that which would be required if the target cell specific ligand were administered alone.

The instant invention is further illustrated by the following Example, which is not intended to limit the invention in any manner.

Example: Construction of Bifunctional Molecule Lys$^3$-bombesin and mAb22 and use Thereof in Inducing Monocyte-Mediated Lysis of Small Cell Cancer of Lung (SCCL) Cells Bispecific molecules comprising Lysine$^3$-bombesin coupled to the human anti-FcγRI monoclonal antibody, mAb 22, were prepared and assayed for their ability to induce antibody dependent effector cell-mediated cytotoxicity (ADCC) against small-cell lung carcinoma (SCCL) cells as follows:

I Materials and Methods

Cell lines: SCCL cell lines, NCI-h69, NCI-H345, and SHP-77 were maintained in RPMI-1640 medium (GIBCO/BRL, Grand Island, N.Y.) supplemented with 5% fetal calf serum (FCS), 2 mM of L-glutamine, 100 units/ml of penicillin, and 100 μg/ml of streptomycin (GIBCO/BRL, Grand Island, N.Y.) at 37° C. in a humidified atmosphere with 5% $CO_2$. Another SCCL cell line, DMS 273 (Ball, E. D. unpublished observation) was maintained in Waymouth's MB 752/1 medium (GIBCO/BRL, Grand Island, N.Y.) supplemented with 10% FCS.

Antibodies and Reagents: Anti-FcγRI (mAb 22), F(ab')$_2$ fragments of mAb 22, and FITC-labeled mAb 22, were obtained from Medarex, Inc. (Annandale, N.J.). SCCL-1, an IgG2a mAb that reacts with the tranferrin receptor on the surface of SCCL cells was produced according to the method of Petroni, et al (1988) J. Immunol. 140:3467–3472. Lysine$^3$-bombesin (Lys-BN), a bombesin (BN) analog with similar binding affinity to the BN/GRP receptor (McDonald, et al. (1979) *Biochem. Biophys. Res. Commun.* 90:227–233, and Spindel, et al. (1984) *Proc. Natl. Acad. Sci. USA.* 81:5699–5703), and hydroxylamine were purchased from Sigma Chemical Company (St. Louis, Mo.). Conjugation chemicals, N-succinimidyl-S-acetyl-thioacetate (SATA) and sulfosuccinimidyl 4-(N-maleimidomethyl) cyclohexane-1-carboxylate (Sulfo-SMCC), were obtained from Pierce Chemical Co. (Rockford, Ill.).

Protein conjugation. FIG. 1 is a schematic illustration of the process used to conjugate $^3$-Lysine and bombesin. The resulting conjugate, Lys-BN, was freshly dissolved in 0.1M sodium phosphate buffer (pH 7.4) containing 2.5 mM EDTA and the SATA was freshly dissolved in 100% dimethylformamide. The SATA was mixed with Lys-BN in a final molar ratio of 10:1. After thirty minutes of reaction at room temperature, the Lys-BN-SATA conjugate was separated from non-reacted Lys-BN and SATA by reverse phase high pressure liquid chromatography (R-HPLC) on a Vydac C18 analytical column. The R-HPLC eluent containing the Lys- BN-SATA was adjusted to pH 4.0–5.0 by adding 1M sodium phosphate (pH 8.0). The free sulfhydryl group was generated by deacetylation with hydroxylamine at 4° C. for two hours. A second R-HPLC was performed to separate Lys-BN-SH. The fraction containing Lys-BN-SH was collected and neutralized to pH 7.0. The presence of free sulfhydryl group could be determined via reaction with Ellman's reagent. At the same time, mAb22 and F(ab')$_2$ fragments of mAb22 were reacted with Sulfo-SMCC to produce a maleimide-activated antibody. The activated antibody was separated from unreacted Sulfo-SMCC by centrifugation through a Centricon 30 apparatus (Amicon, Beverly, Mass.). The final conjugation between Lys-BN-SH and the activated antibody was carried out by mixing at equal molar amount at room temperature overnight. The unreacted Lys-BN-SH and other by-products were removed by centrifugation through a Centricon 30 apparatus. The concentration of the bispecific molecule was quantified using a Bio-Rad DC protein assay (Bio-Rad Laboratories, Richmond, Calif.) and its purity was checked by SDS-PAGE.

Immunofluorescence staining. SCCL cells were washed with ice-cold phosphate buffered saline containing 0.1% bovine serum albumin and 0.1% sodium azide (PBA solution) twice and incubated with different amounts of the bispecific molecule at 4° C. for 1 h in the presence of 100 ug/ml human IgG. The amount of bispecific molecule added was 1, 5, and 10 μg per 5×10$^5$ cells. After washing three times with PBA solution, the cells were resuspended and incubated with FITC-labeled goat F(ab')$_2$ anti-mouse Ig (Caltag Lab., South San Francisco, Calif.) for 30 min at 4° C. After washing, the cells were fixed by addition of PBA solution and 2% paraformaldehyde at 1:1 ratio. Monocytes before and after IFN-γ stimulation were stained directly with FITC-labeled mAb 22 to evaluate the expression of FcγRI.

The binding of the bispecific molecule to SCCL cell lines was analyzed by FACScan flow cytometry (Becton-Dickinson, San Jose, Calif.). The mAb 22 and its F(ab')$_2$ fragments did not stain the SCCL cells by themselves. A typical flow cytometric analysis using the bispecific molecule with four SCCL cell lines is illustrated in FIG. 2. The binding was directly proportional to the amount of bispecific molecule used to stain the cells. This was manifested both by an increase in the absolute percentage of cells stained positively and by an augmentation of the mean fluorescence intensity (MFI) of the entire cell population, as shown in Table 1. As the amount of bispecific molecule was increased from 2.5 μg/ml to 25 μg/ml, the percentage of positive cells increased from 50% to 85%, and the MFI increased from less than 100 to greater than 200. In general, the bispecific molecule prepared between the whole antibody of mAb 22 and Lys-BN had a higher MFI than the one prepared between the F(ab')2 fragments of mab 22 and Lys-BN.

TABLE 1

| Type of IC | Cell line | Conc. (μg/ml) | % pos ± SD | MFI ± SD |
|---|---|---|---|---|
| mAb 22 - BN | NCI-H69 | 2.5 | 49.7 ± 16.6 | 84.90 ± 58.8 (4) |
| | | 10 | 67.9 ± 13.9 | 195.2 ± 108.0 (4) |
| | | 25 | 75.0 ± 7.5 | 234.9 ± 121.5 (4) |
| F(ab')$_2$ -BN | NCI-H69 | 2.5 | 43.9 ± 9.4 | 51.40 ± 15.9 (4) |
| | | 10 | 69.7 ± 9.6 | 112.1 ± 37.9 (4) |
| | | 25 | 75.0 ± 7.7 | 130.8 ± 30.4 (4) |
| mAb 22 - BN | NCI-H35 | 2.5 | 63.6 ± 9.3 | 86.50 ± 24.4 (3) |
| | | 10 | 81.9 ± 7.0 | 224.9 ± 121.1 (3) |
| | | 25 | 84.5 ± 3.3 | 233.7 ± 87.0 (3) |
| F(ab')$_2$ -BN | NCI-H35 | 2.5 | 67.5 ± 6.3 | 57.50 ± 17.7 (3) |

TABLE 1-continued

| Type of IC | Cell line | Conc. (μg/ml) | % pos ± SD | MFI ± SD |
|---|---|---|---|---|
| | | 10 | 80.2 ± 3.3 | 94.10 ± 29.8 (3) |
| | | 25 | 84.9 ± 6.6 | 129.8 ± 10.2 (3) |
| mAb 22 -BN | SHP-77 | 2.5 | 60.0 ± 7.8 | 64.50 ± 14.9 (2) |
| | | 10 | 80.6 ± 5.4 | 204.8 ± 38.4 (2) |
| | | 25 | 85.9 ± 1.6 | 220.6 ± 37.0 (2) |

The binding of the bispecific molecule to normal peripheral lymphocytes and to two leukemia cell lines were also tested. The results are shown in Table 2. The bispecific molecules did not bind to normal peripheral lymphocytes because these cells did not express the FcγRI. The mAb 22 and F(ab')$_2$ fragments of mAb 22 stained both HL-60 and NB4 cells with very dim fluorescence. There was no significant increase in the MFI when they were stained with the bispecific molecule, although the percentage of positive cells increased slightly.

TABLE 2

| Cell | Antibody or IC (25 μ/ml) | % pos | MFI |
|---|---|---|---|
| NB4 cells | mAb 22 | 63.5 | 19.6 |
| | mAb 22 - BN | 62.8 | 20.4 |
| | F(ab')$_2$ | 19.2 | 15.1 |
| | F(ab')$_2$ - BN | 45.3 | 20.1 |
| HL-60 cells | mAb 22 | 17.0 | 20.4 |
| | mAb 22 - BN | 19.5 | 21.8 |
| | F(ab')$_2$ | 1.80 | 18.7 |
| | F(ab')$_2$ - BN | 17.0 | 20.4 |
| Normal lymphocytes | mAb 22 | 1.8 | 5.9 |
| | mAb 22 - BN | 3.8 | 5.7 |
| | F(ab')$_2$ | 0.9 | 6.1 |
| | F(ab')$_2$ - BN | 2.2 | 5.8 |

Isolation of peripheral monocytes. Leuko-Packs were obtained from the Pittsburgh Central Blood Bank. Peripheral mononucleated cells were isolated using Ficoll-Hypaque gradient centrifugation. The mononuclear cells were washed twice with Hanks' balanced salt solution (GIBCO/BRL, Grand Island, N.Y.) containing 1 mM EDTA and then cultured in flask with RPMI-1640 medium containing 10% FCS for 2 h at 37° C. The nonadherent cells were removed. The adherent cells were detached and the purity of isolated monocytes was determined by staining with anti-CD14, anti-CD45, anti-CD3, anti-CD13, and anti-CD56 (Becton-Dickinson). The results were analyzed by FACScan flow cytometry.

Activation of monocytes. Human rIFN-γ was a gift from Dr. Paul Guyer (Dartmouth Medical School, Lebanon, N.H.). The concentration of rIFN-γ used in this study (200 units/ml) has been shown to saturate the receptor for rIFN-γ and to induce a maximal increase in the expression of FcγRI on the surface of monocytes (See Petroni et al. (1988) J. Immunol., 140:3467–3472; Mendel (1990) J. Immunol., 145:267–275). Isolated monocytes were incubated with rIFN-γ in RPMI-1640 medium containing 19% FCS for 18 h at 37° C. before the ADCC assay. The expression of FcγRI on monocytes before and after rIFN-γ incubation was determined by staining with FITC-labeled mAb 22 and analyzed by FACScan flow cytometry.

The binding of the bispecific molecule to peripheral monocytes before and after incubation with 200 units/ml of rIFN-γ for 18 h was also tested. The results are shown in Table 3. rIFN-γ dramatically increased the expression of FcγRI on human monocytes as defined by the increase of MFI from less than 30 to more than 120. In contrast, there was no change in the expression of FcγRI on human peripheral lymphocytes. The conjugation of Lys-BN to the antibody did not interfere with its binding to FcγRI.

TABLE 3

| | Before rIFN-γ I incubation | | After rIFN-γ incubation | |
|---|---|---|---|---|
| | % pos ± SD | MFI ± SD | % pos ± SD | MFI ± SD |
| mAb22 | 83.5 ± 2.2 | 52.0 ± 26.0 (2) | 85.2V16.7 | 210.1 ± 46.7 (2) |
| F(ab')2 | 70.7 ± 15.6 | 29.9 ± 14.6 (2) | 84.7 ± 17.2 | 124.6 ± 25.5 (2) |
| mAb22 - BN | 86.7 ± 3.4 | 25.7 ± 0.10 (2) | 92.1 ± 7.60 | 188.0 ± 85.1 (2) |
| F(ab')2 - BN | 72.3 ± 10.7 | 26.7 ± 8.57 (2) | 85.8 ± 16.3 | 119.6 ± 20.9 (2) |

II Antibody-dependent Effector Cell-mediated Assay

The assay was performed in 96-well round-bottomed microtiter plates (Rainin Instrument Co., Woburn, Mass.). The target SCCL cells were washed once with RPMI-1640 medium and incubated with sodium [$^{51}$ Cr] chromate (New England Nuclear, Boston, Mass.) for 1 h at 37° C. After washing several times, cells were resuspended in RPMI-1640 medium containing 10% FCS to a concentration of $1 \times 10^5$/ml. Activated monocytes serving as effector cells were suspended in RPMI-1640 medium in a final concentration of $2 \times 10^7$/ml. Then, 100 μl of effector cells was added to the first row of wells and serial dilution was performed with equal volume of RPMI-1640 medium. 100 μl of target cells was then added in the wells to yield a final effector:target cell ratio of 100:1, 50:1, 25:1, and 12:1. In a standard assay, 5 μg of the bispecific molecule was finally added. The mAb SCCL-1 was included in each assay as a positive control to measure the activity of the monocytes. Several other controls were also incorporated, including incubation of target and effector cells without any antibody, with irrelevant mouse IgG1, with unconjugated mAb 22, and incubation of target cells with bispecific molecule alone. In some assays, 10-fold excessive amounts of Lys-BN and unconjugated mAb 22 along with the bispecific molecule were incubated together to determine whether the tumor cell lysis could be blocked by either of the parental substance.

The incubation was carried out at 37° C. for 4 h. The microplates were contrifuged and the supernatant was collected for estimation of $^{51}$ Cr release. Maximal lysis was achieved by the addition of 100 μl of 5% NP-40 to 100 μl of target cells. The percentage of cell lysis was calculated as 100×(experimental cpm–spontaneous release mean cpm)/(maximal release mean cpm–spontaneous mean cpm). In all the assays, spontaneous release from the target cells was less than 20% of maximal release. Results were expressed as the mean of triplicate wells.

For dose-response assays, the bispecific molecule was serially diluted and added. The effector to target cell ratio in those assays was 100:1. Since the amount of bispecific molecule added in a standard assay was 25 μg/ml, we defined the percentage of tumor cell lysis achieved with that amount of bispecific molecule as 100% activity. The tumor cell lysis achieved with diluted bispecific molecule was calculated accordingly.

Figure 3:
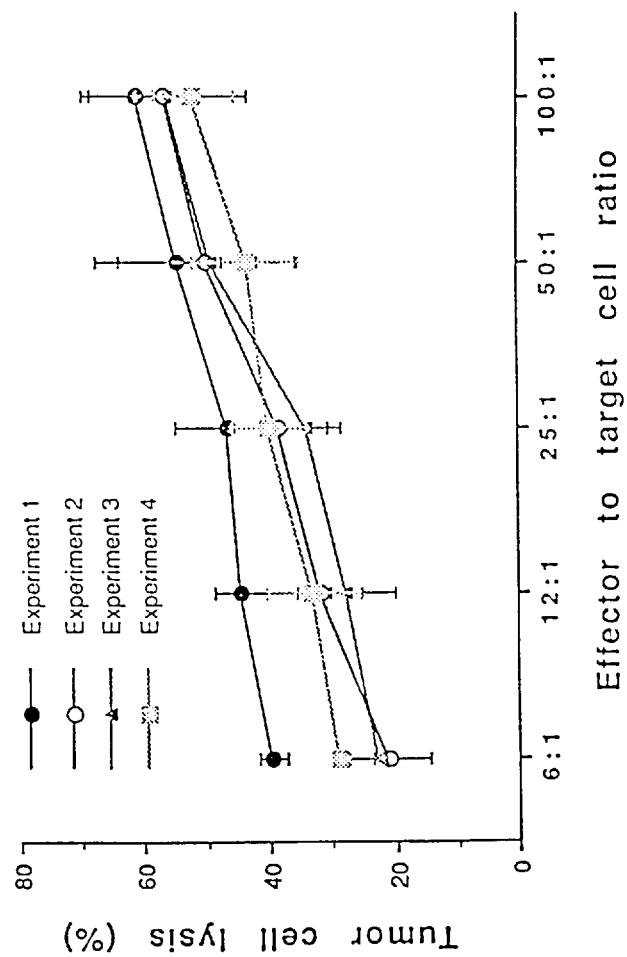
FIG. 3 shows the ability of an bispecific molecule, comprising Lys$^3$-bombesin coupled to mAb 22, to induce lysis, as determined by flow cytometric analysis, of four different SCCL cell lines at various effector cell to target cell ratios. Binding ability is expressed both as an absolute percentage of cells stained and as a mean fluorescence intensity (MFI) of the entire cell population.

The ability of the bispecific molecule to direct monocyte-mediated tumor cell lysis was tested by a series of chromium-releasing assays. The results of three experiments using SHP-77 cell line as target cells are presented in Table 4. Results are expressed as a percentage of total tumor cells lysed. Since the source and preparation of effector cells had an impact on cell lysis, the potency of lysis varied in each experiment. Lysis was dependent on pretreatment of monocytes with rIFN-γ. Without such pretreatment, tumor cell lysis was totally abolished. It was also dependent on effector to target cell ration (E/T ratio). As shown in FIG. 3, an E/T ratio of 100:1, about 60% of tumor cells were consistently lysed. This cell lysis decreased to about 25% at an E/T ratio of 6:1. The mAb 22 itself could induce some nonspecific lysis of SCCL cells in the presence of stimulated monocytes at the highest E/T ratio of 100:1. The addition of Lys-BN did not further increase this nonspecific lysis.

As shown in Table 5, the bispecific molecule induced SCCL cell lysis could be blocked by adding excessive amounts of unconjugated mAb 22 or Lys-BN. Table 5 shows the effect which conjugation of bombesin and mAb 22 and fragments thereof has on tumor cell lysis (SCCL cell line SHP-77), as compared with administration of free bombesin, mAb 22 and fragments thereof. The presence of irrelevant mouse IgG1 had no effect on the results of the assay.

Figure 4:
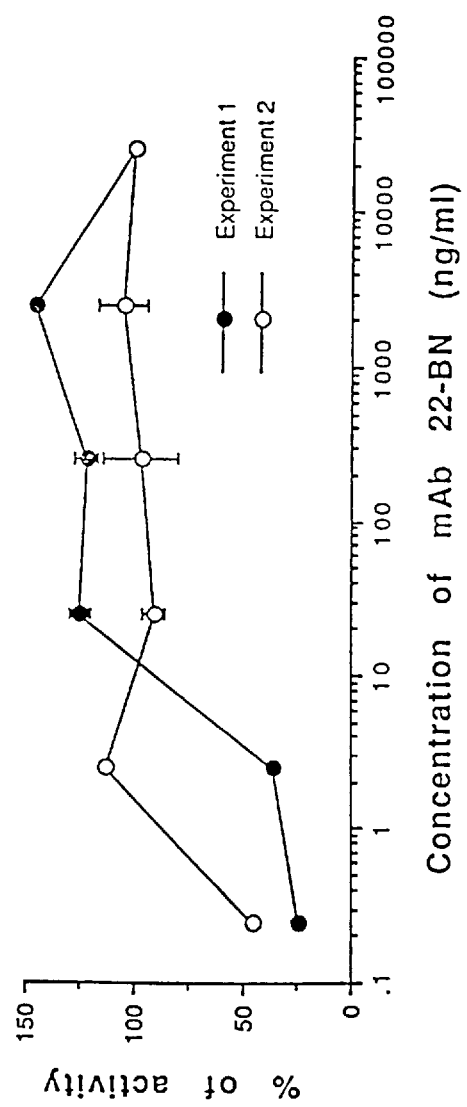
FIG. 4 shows the ability of various concentrations of bispecific molecule (Lys$^3$-bombesin-mAb 22) to induce lysis of SCCL cells from the cell line SHP-77. The peak of activity to mediate tumor cell lysis was seen in a wide range of bispecific molecule concentrations ranging from 25 to 25,000 ng/ml.

Dose response assays were also performed to test the ability of various concentrations of bispecific molecule to induce lysis of SCCL cells. The results of two such experiments are shown in FIG. 4. The peak of activity to mediate tumor cell lysis was seen in a wide range of concentrations of the bispecific molecule between 25 to 25000 ng/ml.

TABLE 4

| | Type of IC | E:T ratio | % lysis ± SD |
|---|---|---|---|
| Experiment 1 | mAb22-BN | 100:1 | 60.9 ± 7.7 |
| | | 50:1 | 54.6 ± 12.9 |
| | | 25:1 | 46.6 ± 8.3 |
| | | 12.1 | 44.6 ± 4.1 |
| | | 6:1 | 39.4 ± 2.3 |
| Experiment 2 | mAb22-BN | 100:1 | 56.4 ± 13.1 |
| | | 50:1 | 49.7 ± 14.3 |
| | | 25:1 | 38.4 ± 7.9 |
| | | 12:1 | 31.8 ± 1.5 |
| | | 6:1 | 39.4 ± 2.3 |
| Experiment 3 | mAb22-BN | 100:1 | 56.2 ± 4.7 |
| | | 50:1 | 49.1 ± 1.8 |
| | | 25:1 | 33.7 ± 5.3 |
| | | 12:1 | 27.7 ± 7.7 |
| | | 6:1 | 22.5 ± 0.9 |
| | F(ab)2-BN | 100:1 | 51.9 ± 6.4 |
| | | 50:1 | 43.5 ± 8.6 |
| | | 25:1 | 39.5 ± 6.1 |
| | | 12:1 | 32.8 ± 7.6 |
| | | 6:1 | 28.7 ± 1.6 |

TABLE 5

| Incubation condition | % lysis ± SD |
|---|---|
| No monocytes | 0.1 ± 0.1 |
| mAb 22 + monocytes | 27.0 ± 1.6 |
| mAb 22 + BN + monocytes | 24.4 ± 2.6 |
| SCCL-1 + monocytes | 50.9 ± 0.4 |
| mAb 22-BN + monocytes | 49.1 ± 1.8 |
| mAb 22-BN + BN + monocytes | 33.6 ± 3.2 |
| mAb 22-BN + mAb 22 + monocytes | 35.0 ± 2.0 |
| F(ab')2 + monocytes | 14.0 ± 1.9 |
| F(ab')2 + BN + monocytes | 21.0 ± 1.3 |
| SCCL-1 + monocytes | 38.0 ± 0.7 |
| F(ab')2-BN + monocytes | 43.5 ± 8.6 |
| F(ab')2-BN + BN + monocytes | 24.2 ± 0.6 |
| F(ab')2-BN + F(ab')2 + monocytes | 31.8 ± 5.6 |

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

We claim:

1. A tumor cell-specific effector cell comprising:
   (i) an effector cell;
   (ii) a non-immunoglobulin tumor cell-specific ligand; and
   (iii) an antibody selected from the group consisting of: mAb22 produced by the hybridoma having ATCC Accession number HB12147 and mAb32 produced by the hybridoma having ATCC number HB9469.

2. The tumor cell-specific effector cell of claim 1, wherein the ligand is selected from the group consisting of bombesin and gastrin-releasing peptide.

3. A method of inducing a specific antibody dependent effector cell-mediated cytotoxicity against a tumor cell, in a subject, comprising administering to the subject a bispecific molecule comprising (a) a non-immunoglobulin tumor cell-specific ligand, and (b) an antibody selected from the group consisting of: mAb22 produced by the hybridoma having ATCC Accession number HB12147 and mAb32 produced by the hybridoma having ATCC number HB9469.

4. The method of claim 3 wherein the ligand is selected from the group consisting of bombesin and gastrin-releasing peptide.

5. A bispecific molecule comprising a non-immunoglobulin tumor cell-specific ligand and an antibody selected from the group consisting of: mAb22 produced by the hybridoma having ATCC Accession number HB12147 and mAb32 produced by the hybridoma having ATCC number HB9469.

6. The bispecific molecule of claim 5 wherein the ligand is selected from the group consisting of bombesin and gastrin-releasing peptide.

7. A bispecific molecule comprising bombesin or an analogue thereof and mAb22 produced by the hybridoma having ATCC Accession number HB12147.

8. A bispecific molecule comprising bombesin or an analogue thereof and mAb32 produced by the hybridoma having ATCC Accession number HB9469.

* * * * *